United States Patent [19]

Tucker

[11] Patent Number: 4,636,505

[45] Date of Patent: Jan. 13, 1987

[54] AMIDE DERIVATIVES

[75] Inventor: Howard Tucker, Macclesfield, United Kingdom

[73] Assignee: Imperial Chemical Industries PLC, London, England

[21] Appl. No.: 514,332

[22] Filed: Jul. 15, 1983

[30] Foreign Application Priority Data

Jul. 23, 1982 [GB] United Kingdom ............... 8221421

[51] Int. Cl.$^4$ ................ A61K 31/505; A61K 31/275; A61K 31/16
[52] U.S. Cl. .................... 514/256; 544/316; 544/335; 548/503; 546/141; 546/145; 548/550; 546/146; 546/172; 548/556; 546/175; 546/291; 548/125; 546/330; 546/337; 548/142; 514/274; 514/307; 548/171; 514/311; 514/346; 548/180; 514/357; 514/359; 548/202; 514/361; 514/363; 548/204; 514/365; 514/367; 548/255; 514/369; 514/394; 548/262; 514/398; 514/400; 548/265; 514/415; 514/424; 548/325; 514/427; 514/438; 548/337; 514/443; 514/445; 548/343; 514/469; 514/470; 549/55; 514/471; 514/522; 549/65; 514/546; 514/618; 549/76; 514/625; 514/627; 549/466; 549/467; 549/475; 549/493; 558/413; 558/414; 560/250; 564/162; 564/191; 564/192; 564/202; 564/207; 564/214; 514/628
[58] Field of Search ............... 564/165, 170, 162, 191, 564/192, 202, 207, 214; 260/465 D; 514/256, 274, 307, 311, 346, 357, 359, 361, 363, 365, 367, 369, 394, 398, 400, 415, 424, 427, 438, 443, 445, 469, 470, 471, 522, 546, 618, 628; 544/316, 335; 546/141, 145, 146, 172, 175, 291, 330, 337; 548/125, 142, 171, 180, 202, 204, 255, 262, 265, 325, 337, 343, 503, 550, 556; 549/55, 65, 76, 466, 467, 475, 493; 558/413, 414; 560/250

[56] References Cited

U.S. PATENT DOCUMENTS

| 3,875,229 | 4/1975 | Gold | 260/562 R |
|---|---|---|---|
| 3,995,060 | 11/1976 | Neri et al. | 424/324 |
| 4,039,684 | 8/1977 | Berkman et al. | 424/324 |
| 4,139,638 | 2/1979 | Neri et al. | 424/324 |
| 4,144,270 | 3/1979 | Neri et al. | 260/562 R |
| 4,191,775 | 3/1980 | Glen | 564/202 X |
| 4,239,776 | 12/1980 | Glen et al. | 424/304 |
| 4,282,218 | 8/1981 | Glen et al. | 424/240 |
| 4,329,364 | 5/1982 | Neri et al. | 424/324 |
| 4,386,080 | 5/1983 | Crossley et al. | 564/162 X |

FOREIGN PATENT DOCUMENTS 52-128329 10/1977 Japan.
1287753 9/1972 United Kingdom.

Primary Examiner—Dolph H. Torrence
Attorney, Agent, or Firm—Cushman, Darby & Cushman

[57] ABSTRACT

Acylanilides of the formula

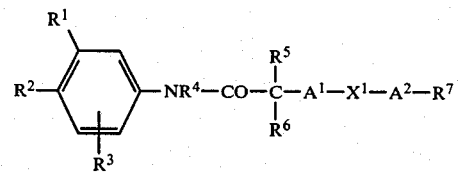

wherein
$R^1$ and $R^2$, the same or different, each is cyano, carbamoyl, nitro, halogeno, perfluoroalkyl or other defined substituents;
$R^3$ is hydrogen or halogen;
$R^4$ is hydrogen or alkyl, or is joined to $R^5$;
$R^5$ is hydrogen, hydroxy, alkoxy or acyloxy or is joined to $R^4$;
$R^6$ is alkyl or halogenoalkyl, or has the formula —$A^3$—$R^8$ or —$A^4$—$X^2$—$A^5$—$R^9$;
$A^1$ and $A^4$, the same or different, each is alkylene;
$A^2$, $A^3$ and $A^5$, the same or different, each is a direct link or alkylene;
$X^1$ and $X^2$, the same or different, each is oxygen, sulphur, sulphinyl, sulphonyl, imino or alkylimino;
$R^7$ and $R^9$, the same or different, each is alkyl, alkenyl, hydroxyalkyl, cycloalkyl, phenyl optionally substituted, naphthyl or heterocyclic optionally substituted;
and $R^8$ is phenyl, naphthyl or heterocyclic as defined above for $R^7$ or $R^9$; processes for their manufacture and pharmaceutical compositions containing them. The acylanilides possess antiandrogenic activity.

9 Claims, No Drawings

AMIDE DERIVATIVES

This invention relates to new amide derivatives and more particularly it relates to novel acylanilides which possess antiandrogenic properties.

Many acylanilides are known which possess antiandrogenic activity. In particular, the compound of the formula:

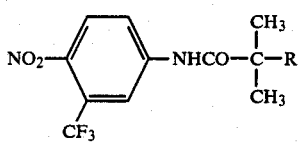

wherein R is hydrogen, which compound is known as FLUTAMIDE, is under development for use as an antiandrogen. It is believed that flutamide is oxidised in vivo to the corresponding compound wherein R is hydroxy.

Other acylanilides which possess antiandrogenic activity are known from European Specifications Nos. 2309, 2892 and 40932, and from Japanese Specification No. 52-128329.

According to the present invention there is provided an acylanilide of the formula:

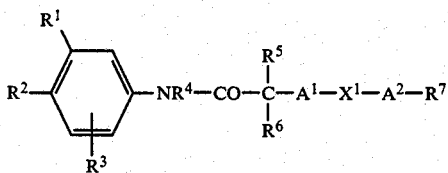

wherein $R^1$ is cyano, carbamoyl, nitro, fluoro, chloro, bromo, iodo or hydrogen, or alkyl, alkoxy, alkanoyl, alkylthio, alkylsulphinyl, alkylsulphonyl, perfluoroalkyl, perfluoroalkylthio, perfluoroalkylsulphinyl or perfluoroalkylsulphonyl each of up to 4 carbon atoms, or phenylthio, phenylsulphinyl or phenylsulphonyl;
wherein $R^2$ is cyano, carbamoyl, nitro, fluoro, chloro, bromo or iodo, or alkanoyl, alkylthio, alkylsulphinyl, alkylsulphonyl, perfluoroalkyl, perfluoroalkylthio, perfluoroalkylsulphinyl or perfluoroalkylsulphonyl each of up to 4 carbon atoms, or phenylthio, phenylsulphinyl or phenylsulphonyl;
wherein $R^3$ is hydrogen or halogen;
wherein $R^4$ is hydrogen or alkyl of up to 4 carbon atoms, or is joined to $R^5$ as stated below;
wherein $R^5$ is hydrogen, hydroxy or alkoxy or acyloxy each of up to 15 carbon atoms, or is joined to $R^4$ to form an oxycarbonyl group such that together with the —N—CO—C— part of the molecule it forms an oxazolidinedione group;
wherein $R^6$ is alkyl or halogenoalkyl of up to 4 carbon atoms, or has the formula —$A^3$—$R^8$ or —$A^4$—$X^2$—$A^5$—$R^9$;
wherein $A^1$ and $A^4$, which may be the same or different, each is alkylene of up to 6 carbon atoms;
wherein $A^2$, $A^3$ and $A^5$, which may be the same or different, each is a direct link or alkylene of up to 6 carbon atoms;
wherein $X^1$ and $X^2$, which may be the same or different, each is oxygen, sulphur, sulphinyl (—SO—), sulphonyl (—$SO_2$—), imino (—NH—) or alkylimino (—$NR^{10}$— wherein $R^{10}$ is alkyl of up to 6 carbon atoms);
wherein $R^7$ and $R^9$, which may be the same or different, each is alkyl, alkenyl, hydroxyalkyl or cycloalkyl each of up to 6 carbon atoms, or $R^7$ or $R^9$ is phenyl which bears one, two or three substituents selected from hydrogen, halogen, nitro, carboxy, carbamoyl and cyano, and alkyl, alkoxy, alkanoyl, alkylthio, alkylsulphinyl, alkylsulphonyl, perfluoroalkyl, perfluoroalkylthio, perfluoroalkylsulphinyl, perfluoroalkylsulphonyl, alkoxycarbonyl and N-alkylcarbamoyl each of up to 4 carbon atoms, and phenyl, phenylthio, phenylsulphinyl and phenylsulphonyl; or $R^7$ or $R^9$ is naphthyl; or $R^7$ or $R^9$ is 5- or 6-membered saturated or unsaturated heterocyclic which contains one, two or three heteroatoms selected from oxygen, nitrogen and sulphur, which heterocyclic may be a single ring or may be fused to a benzo-ring, and which heterocyclic is unsubstituted or bears one or two halogen, cyano or amino, or alkyl, alkoxy, alkylthio, alkylsulphinyl or alkylsulphonyl each of up to 4 carbon atoms, or oxy or hydroxy substituents, or which if sufficiently saturated may bear one or two oxo substituents; and wherein $R^8$ is phenyl, naphthyl or heterocyclic as defined above for $R^7$ or $R^9$.

It will be observed that the acylanilide derivative of the invention possesses an asymmetric carbon atom, namely the carbon atom which bears the substituents $R^5$ and $R^6$, and it can therefore exist in racemic and optically-active forms. It is to be understood that this invention encompasses the racemic form of the acylanilide derivative and any optically-active form which possesses antiandrogenic activity, it being a matter of common general knowledge how a racemic compound may be resolved into its optically-active forms and how any antiandrogenic activity present in any of these forms may be determined.

A suitable value for $R^1$, $R^4$ or $R^{10}$ when it is alkyl, or for an alkyl substituent in $R^7$, $R^8$ or $R^9$ when $R^7$, $R^8$ or $R^9$ is phenyl or heterocyclic substituted by alkyl is, for example, methyl or ethyl.

A suitable value for $R^1$ when it is alkoxy, or for an alkoxy substituent in $R^7$, $R^8$ or $R^9$ when $R^7$, $R^8$ or $R^9$ is phenyl or heterocyclic substituted by alkoxy is, for example, methoxy or ethoxy.

A suitable value for $R^1$ or $R^2$ when it is alkanoyl, or for an alkanoyl substituent in $R^7$, $R^8$ or $R^9$ when $R^7$, $R^8$ or $R^9$ is phenyl substituted by alkanoyl is, for example, formyl or acetyl.

A suitable value for $R^1$ or $R^2$ when it is alkylthio, alkylsulphinyl, alkylsulphonyl, perfluoroalkyl, perfluoroalkylthio, perfluoroalkylsulphinyl or perfluoroalkylsulphonyl, or for such a substituent in $R^7$, $R^8$ or $R^9$ when $R^7$, $R^8$ or $R^9$ is phenyl or heterocyclic bearing such a substituent is, for example, methylthio, ethylthio, methylsulphinyl, methylsulphonyl, trifluoromethyl, pentafluoroethyl, trifluoromethylthio, trifluoromethylsulphinyl or trifluoromethylsulphonyl.

A suitable value for $R^3$ when it is halogen, or for a halogen substituent in $R^7$, $R^8$ or $R^9$ when $R^7$, $R^8$ or $R^9$ is phenyl or heterocyclic substituted by halogen, is fluoro, chloro, bromo or iodo.

$R^3$ is preferably hydrogen or chloro, especially hydrogen.

$R^4$ is preferably hydrogen.

A suitable value for an alkoxycarbonyl or N-alkylcarbamoyl substituent in $R^7$, $R^8$ or $R^9$ when $R^7$, $R^8$ or $R^9$ is phenyl bearing such a substituent is, for example, methoxycarbonyl, ethoxycarbonyl or N-methylcarbamoyl.

A suitable value for $R^5$ when it is alkoxy is, for example, methoxy, ethoxy, propyloxy, n-butyloxy or decyloxy.

A suitable value for $R^5$ when it is acyloxy is, for example, alkanoyloxy or aroyloxy each of up to 15 carbon atoms, for example acetoxy, propionyloxy, decanoyloxy, dodecanoyloxy or benzoyloxy.

$R^5$ is preferably hydroxy.

A suitable value for $R^6$ when it is alkyl or halogenoalkyl is, for example, methyl, ethyl, n-propyl, fluoromethyl, difluoromethyl, trifluoromethyl, pentafluoroethyl, chloromethyl, dichloromethyl or trichloromethyl. $R^6$ is preferably methyl or trifluoromethyl, especially methyl.

A suitable value for $A^1$, $A^2$, $A^3$, $A^4$, or $A^5$ when it is alkylene is, for example, methylene, ethylene, ethylidene

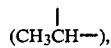

trimethylene, tetramethylene,

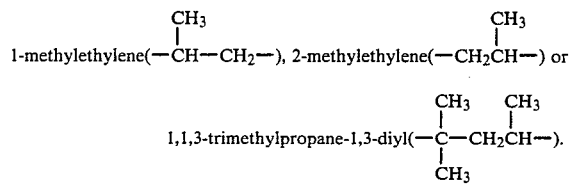

A suitable value for $R^7$ or $R^9$ when it is alkyl, alkenyl, hydroxyalkyl or cycloalkyl is, for example, methyl, ethyl, n-propyl, isopropyl, n-butyl, allyl, 2-methylprop-2-enyl, 2-hydroxyethyl, cyclopentyl or cyclohexyl.

A suitable value for $R^7$, $R^8$ or $R^9$ when it is heterocyclic is, for example, furyl, thienyl, pyrrolyl, pyridyl, imidazolyl, thiazolyl, pyrimidinyl, thiadiazolyl, triazolyl, benzimidazolyl, benzothiazolyl, indolyl, benzothienyl, benzofuryl, quinolyl, isoquinolyl or 1,2-dihydro-2-oxoquinolyl.

A preferred combination of values for $R^1$ and $R^2$ is as follows:

| $R^1$ | $R^2$ |
| --- | --- |
| trifluoromethyl | nitro |
| trifluoromethyl | cyano |
| chloro | chloro |
| chloro | nitro |
| chloro | cyano |
| cyano | cyano |

A preferred acylanilide of the invention has the formula stated above wherein $R^1$ is cyano, nitro, trifluoromethyl, chloro, methyl or methoxy, $R^2$ is cyano, nitro, trifluoromethyl or chloro, $R^3$ and $R^4$ are both hydrogen, $R^5$ is hydroxy, $R^6$ is methyl or trifluoromethyl, $A^1$ is methylene, ethylene or ethylidene, $X^1$ is oxygen, sulphur, sulphinyl, sulphonyl, imino or methylimino, $A^2$ is a direct link or methylene and $R^7$ is alkyl, alkenyl, hydroxyalkyl or cycloalkyl each of up to 6 carbon atoms, or phenyl which is unsubstituted or which bears one fluoro, chloro, cyano, nitro, methoxy or methylthio substituent, or thienyl, imidazolyl, thiazolyl, benzothiazolyl, thiadiazolyl, pyridyl or pyrimidinyl which is unsubstituted or which bears one chloro, bromo or methyl substituent.

A particularly preferred acylanilide of the invention has the formula stated above wherein $R^1$ is trifluoromethyl, $R^2$ is cyano or nitro, $R^3$ and $R^4$ are both hydrogen, $R^5$ is hydroxy, $R^6$ is methyl, $A^1$ is methylene, $X^1$ is sulphur, sulphinyl or sulphonyl, $A^2$ is a direct link and $R^7$ is alkyl of up to 3 carbon atoms, especially ethyl, or is allyl, phenyl, p-fluorophenyl, thiazol-2-yl, 4-methylthiazol-2-yl, 5-methyl-1,3,4-thiadiazol-2-yl or 2-pyridyl.

Specific acylanilides of the invention are hereinafter described in the Examples.

Particularly active compounds are 3-chloro-4-cyano-N-(3-ethylthio-2-hydroxy-2-methylpropionyl)aniline;

3-chloro-4-cyano-N-(3-ethylsulphonyl-2-hydroxy-2-methylpropionyl)aniline;

4-cyano-3-trifluoromethyl-N-(2-hydroxy-2-methyl-3-phenylsulphonylpropionyl)aniline;

4-cyano-3-trifluoromethyl-N-(3-ethylsulphonyl-2-hydroxy-2-methylpropionyl)aniline;

4-nitro-3-trifluoromethyl-N-(2-hydroxy-3-phenylsulphonyl-2-methylpropionyl)aniline;

4-nitro-3-trifluoromethyl-N-(3-ethylsulphonyl-2-hydroxy-2-methylpropionyl)aniline;

3-chloro-4-nitro-N-(2-hydroxy-3-phenylthio-2-methylpropionyl)aniline;

4-nitro-3-trifluoromethyl-N-[2-hydroxy-2-methyl-3-(thiazol-2-ylthio)propionyl]aniline;

4-nitro-3-trifluoromethyl-N-[3-allylthio-2-hydroxy-2-methylpropionyl)aniline;

4-nitro-3-trifluoromethyl-N-(3-p-fluorophenylthio-2-hydroxy-2-methylpropionyl)aniline;

4-nitro-3-trifluoromethyl-N-[2-hydroxy-2-methyl-3-(pyrid-2-ylthio)propionyl]aniline;

4-nitro-3-trifluoromethyl-N-[2-hydroxy-2-methyl-3-(5-methyl-1,3,4-thiadiazol-2-ylthio)propionyl]aniline;

4-nitro-3-trifluoromethyl-N-[2-hydroxy-2-methyl-3-(4-methylthiazol-2-ylthio)propionyl]aniline;

4-nitro-3-trifluoromethyl-N-[2-hydroxy-2-methyl-3-(pyrid-2-ylsulphonyl)propionyl]aniline;

4-nitro-3-trifluoromethyl-N-(3-p-fluorophenylsulphonyl-2-hydroxy-2-methylpropionyl)aniline;

4-cyano-3-trifluoromethyl-N-[2-hydroxy-2-methyl-3-(thiazol-2-ylthio)propionyl]aniline;

4-cyano-3-trifluoromethyl-N-[2-hydroxy-2-methyl-3-(pyrid-2-ylthio)propionyl]aniline;

4-cyano-3-trifluoromethyl-N-(2-hydroxy-2-methyl-3-methylthiopropionyl)aniline;

4-cyano-3-trifluoromethyl-N-(3-p-fluorophenylthio-2-hydroxy-2-methylpropionyl)aniline; and 4-cyano-3-trifluoromethyl-N-(3-p-fluorophenylsulphonyl-2-hydroxy-2-methylpropionyl)aniline;

and of these the last-mentioned is especially preferred.

The acylanilides of the invention may be manufactured by any chemical process known to be suitable for the manufacture of chemically-analogous compounds.

One preferred process for the manufacture of an acylanilide of the invention comprises the reaction of an amine of the formula:

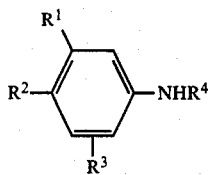

wherein $R^1$, $R^2$, $R^3$ and $R^4$ have the meanings stated above, with an acid of the formula:

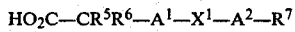

wherein $R^5$, $R^6$, $R^7$, $X^1$, $A^1$ and $A^2$ have the meanings stated above, or with a reactive derivative of said acid.

A suitable reactive derivative of an acid is, for example, an acid anhydride, or an acyl halide, for example an acyl chloride, or a lower alkyl ester of said acid, for example the methyl or ethyl ester. Preferably the reaction is carried out in N,N-dimethylacetamide solution using an acyl chloride (prepared from the acid and thionyl chloride) as reactant.

A second preferred process for the manufacture of an acylanilide of the invention wherein $R^5$ is hydroxy and $X^1$ is sulphur or alkylimino comprises the reaction of an epoxide of the formula:

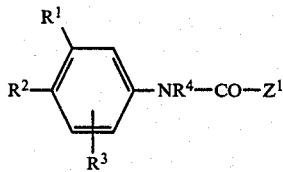

wherein $R^1$, $R^2$, $R^3$ and $R^4$ have the meanings stated above and wherein $Z^1$ has the formula

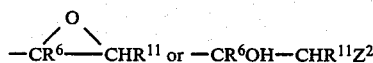

wherein $R^6$ has the meaning stated above, wherein $Z^2$ is a displaceable group and wherein $R^{11}$ is such that —$CHR^{11}$— is —$A^1$— as stated above, with a thiol or amine of the formula:
$R^7$—$A^2$—SH or $R^7$—$A^2$—$NHR^{10}$ wherein $R^7$, $R^{10}$ and $A^2$ have the meanings stated above.

A suitable value for $Z^2$ is, for example, a halogeno or sulphonyloxy group, for example the chloro, bromo, iodo, methanesulphonyloxy or p-toluenesulphonyloxy group. The abovementioned reaction is preferably carried out in an inert diluent or solvent, for example tetrahydrofuran, and in the presence of a base, for example sodium hydride.

The epoxide used as starting material may be obtained by the epoxidation, for example with a per-acid, of the corresponding unsaturated acylanilide.

A third preferred process for the manufacture of an acylanilide of the invention wherein $R^5$ is hydroxy comprises the reaction of a compound of the formula:

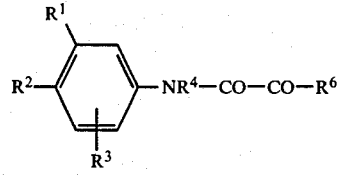

wherein $R^1$, $R^2$, $R^3$, $R^4$ and $R^6$ have the meanings stated above, with an organometallic compound of the formula

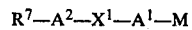

wherein $A^1$, $A^2$, $R^7$ and $X^1$ have the meanings stated above and M is a metal radical, for example the lithium radical.

The last-mentioned reaction is preferably carried out in an inert solvent, for example diethyl ether or tetrahydrofuran, at a low temperature, for example at between $-60°$ C. and $-100°$ C.

An acylanilide of the invention wherein $R^4$ and $R^5$ are joined together to form a carbonyloxy group, that is, an oxazolidinedione, may be prepared by the reaction of an isocyanate of the formula:

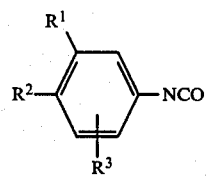

wherein $R^1$, $R^2$ and $R^3$ have the meanings stated above, with an ester of the formula:

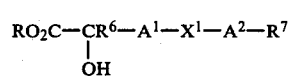

wherein $R^6$, $R^7$, $X^1$, $A^1$ and $A^2$ have the meanings stated above, and wherein R is alkyl of up to 6 carbon atoms, for example methyl or ethyl. This reaction is preferably carried out in an organic solvent, for example diethyl ether, at laboratory temperature.

An acylanilide of the invention wherein $R^5$ is hydroxy may be prepared by the hydrolysis of the corresponding acylanilide wherein $R^5$ is acyloxy, and an acylanilide of the invention wherein $R^5$ is hydroxy and $R^4$ is hydrogen may be prepared by the hydrolysis of the corresponding oxazolidinedione, which may be prepared as described in the preceding paragraph.

An acylanilide of the invention wherein $R^4$ is alkyl may be prepared by the alkylation of the corresponding acylanilide wherein $R^4$ is hydrogen.

An acylanilide of the invention wherein $R^5$ is acyloxy may be prepared by the acylation of the corresponding acylanilide wherein $R^5$ is hydroxy.

An oxazolidinedione of the invention, wherein $R^4$ and $R^5$ are joined together to form a carbonyloxy group, may be prepared by the reaction of the corresponding acylanilide wherein $R^4$ is hydrogen and $R^5$ is hydroxy with phosgene ($COCl_2$).

An acylanilide of the invention wherein $X^1$ or $X^2$ is sulphinyl or sulphonyl or wherein one or more of $R^1$, $R^2$ and a substituent in the phenyl or heterocyclic group $R^7$, $R^8$ or $R^9$ is alkylsulphinyl, perfluoroalkylsulphinyl or phenylsulphinyl, or is alkylsulphonyl, perfluoroalkylsulphonyl or phenylsulphonyl, may be prepared by the oxidation of the corresponding acylanilide wherein $X^1$ or $X^2$ is sulphur or wherein one or more of $R^1$, $R^2$ and a substituent in the phenyl or heterocyclic group $R^7$, $R^8$ or $R^9$ is alkylthio, perfluoroalkylthio or phenylthio, respectively. The oxidising agent and conditions used will determine whether a sulphinyl or a sulphonyl compound is obtained. Thus, oxidation with sodium metaperiodate in methanol solution at or below laboratory temperature will generally convert a thio compound into the corresponding sulphinyl compound; and oxidation with a per-acid, for example m-chloroperbenzoic acid, in methylene chloride solution at or above laboratory temperature will generally convert a thio compound into the corresponding sulphonyl compound.

A racemic acylanilide of the invention wherein $R^5$ is hydroxy may be separated into its optical isomers by forming an ester of the hydroxy group $R^5$ with an optically-active acid, for example (−)-camphanic acid, separating the diastereoisomeric esters thus obtained, by fractional crystallisation or, preferably, by flash-chromatography, and then hydrolysing each separate ester to the alcohol. Alternatively, an optically active acylanilide of the invention may be obtained by using any of the processes described above with an optically-active starting material.

As stated above, an acylanilide of the invention possesses antiandrogenic properties as demonstrated by its ability to decrease the weight of the seminal vesicles of a mature male rat when administered orally for 4 successive days. An acylanilide of the invention may therefore be used in the treatment of, for example, malignant or benign prostatic disease or of androgen dependent disease conditions, such as acne, hirsutism or seborrhoea, in warm-blooded vertebrates including man. It may also be used to improve ovulation in a domestic animal.

A preferred acylanilide of the invention is up to 10 times more active as an antiandrogen than the known, chemically-related antiandrogens flutamide and hydroxyflutamide. At a dose of an acylanilide of the invention which produces antiandrogenic activity in rats no symptoms of toxicity are apparent.

The acylanilide of the invention may be administered to a warm-blooded animal in the form of a pharmaceutical or veterinary composition which comprises the acylanilide in association with a pharmaceutically-acceptable diluent or carrier.

The composition may be in a form suitable for oral dosage, as a tablet, capsule, aqueous or oily solution or suspension or emulsion. It may alternatively be in the form of a sterile solution or suspension suitable for parenteral administration, or be in the form of an ointment or lotion for topical administration, or be in the form of a suppository for anal or vaginal administration.

The composition may additionally contain one or more drugs selected from anti-oestrogens, for example tamoxifen; aromatase inhibitors, for example testolactone or aminoglutethamide; progestins, for example medroxyprogesterone acetate; inhibitors of gonadotrophin secretion, for example danazol; LH-RH-analogues, for example buserelin; cytotoxic agents, for example cyclophosphamide; antibiotics, for example penicillin or oxytetracyclin; and anti-inflammatory agents, for example, especially for topical use, fluocinolone acetonide.

The acylanilide of the invention will normally be administered to a warm-blooded animal at a dose of between 0.1 mg. and 125 mg. per kg. bodyweight.

The invention is illustrated but not limited by the following Examples:

EXAMPLE 1

Thionyl chloride (0.6 ml.) was added to a stirred solution of 2-hydroxy-2-methyl-3-phenylthiopropionic acid (1.7 g.) in N,N-dimethylacetamide (40 ml.) which was cooled to −15° C., at such a rate that that temperature was maintained, and the mixture was stirred at that temperature for 15 minutes. 4-Cyano-3-trifluoromethylaniline (1.5 g.) was added, the mixture was stirred at −15° C. for 30 minutes and then at laboratory temperature for 15 hours, and was then poured into water (800 ml.). The mixture was extracted six times with diethyl ether (80 ml. each time) and the combined extracts were washed successively (50 ml. portions each time) twice with aqueous 3N-hydrochloric acid, once with saturated aqueous sodium chloride solution, twice with saturated aqueous sodium bicarbonate solution, and again once with saturated aqueous sodium chloride solution, dried over magnesium sulphate and evaporated to dryness under reduced pressure. The residue was purified by chromatography on a silica gel column (Merck 7734) using methylene chloride as eluant. The product was crystallised from a 5:1 v/v mixture of toluene and petroleum ether (b.p. 60°–80° C.) and there was thus obtained 4-cyano-3-trifluoromethyl-N-(2-hydroxy-2-methyl-3-phenylthiopropionyl)aniline, m.p. 81.5°–83° C.

The 2-hydroxy-2-methyl-3-phenylthiopropionic acid used as starting material was obtained as follows:

Route A

A solution of methyl 2,3-epoxy-2-methylpropionate (4.06 g.) in tetrahydrofuran (40 ml.) was added during 20 minutes to a stirred suspension of thiophenol (7.7 g.) and sodium hydride (2.9 g. of a 60% dispersion in mineral oil) in tetrahydrofuran (75 ml.) which was maintained under an atmosphere of nitrogen, and the mixture was stirred at laboratory temperature for 15 minutes, then at 60° C. for 4 hours, cooled and neutralised by dropwise addition of a solution of concentrated sulphuric acid (0.5 ml.) in ethanol (5 ml.) A solution of potassium hydroxide (10 g.) in a mixture of water (30 ml.) and ethanol (150 ml.) was added and the mixture was heated under reflux for 22 hours. The organic solvents were removed by evaporation under reduced pressure, water (50 ml.) was added and the mixture was washed twice with diethyl ether (25 ml. each time). The aqueous solution was then acidified with concentrated aqueous hydrochloric acid and extracted four times with diethyl ether (100 ml. each time). The combined extracts were washed with saturated aqueous sodium chloride solution (50 ml.), dried over magnesium sulphate and evaporated to dryness, and the residue was crystallised from a 5:1 v/v mixture of petroleum ether (b.p. 60°–80° C.) and toluene. There was thus obtained 2-hydroxy-2-methyl-3-phenylthiopropionic acid, m.p. 95.5°–97° C.

EXAMPLE 2

The process described in Example 1 was repeated except that the appropriate aniline and the appropriate 2-hydroxy-substituted-alkanoic acid were used as starting materials. There were thus obtained the compounds described in the following table:

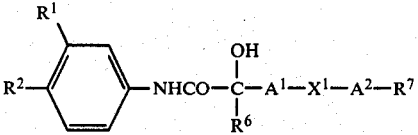

| R¹ | R² | R⁶ | A¹ | X¹ | A² | R⁷ | m.p. (°C.) |
|---|---|---|---|---|---|---|---|
| CF₃ | NO₂ | CH₃ | CH₂ | S | — | phenyl | 105–106 |
| CF₃ | NO₂ | CH₃ | CH₂ | S | — | 2-nitrophenyl | 52–54 |
| CF₃ | NO₂ | CH₃ | CH₂ | S | — | methyl | 109–110 |
| CF₃ | NO₂ | CH₃ | CH₂ | S | — | ethyl | (gum) |
| CF₃ | NO₂ | CH₃ | CH₂ | S | — | n-propyl | (gum) |
| CF₃ | NO₂ | CH₃ | CH₂ | S | — | isopropyl | 66–68 |
| CF₃ | CN | CH₃ | CH₂ | S | — | ethyl | (gum) |
| CF₃ | CN | CH₃ | CH₂ | S | — | n-propyl | (gum) |
| CF₃ | CN | CH₃ | CH₂ | S | — | isopropyl | 98–100 |
| CF₃ | CN | CH₃ | CH₂ | S | — | methyl | 108.5–109.5 |
| CN | CN | CH₃ | CH₂ | S | — | phenyl | 82–83.5 |
| Cl | Cl | CH₃ | CH₂ | S | — | methyl | 90.5–91.5 |
| Cl | CN | CH₃ | CH₂ | S | — | phenyl | 60–62 |
| Cl | CN | CH₃ | CH₂ | S | — | ethyl | 96–98 |
| NO₂ | Cl | CH₃ | CH₂ | S | — | phenyl | 77–78 |
| Cl | NO₂ | CH₃ | CH₂ | S | — | phenyl | 88–90 |
| Cl | NO₂ | CH₃ | CH₂ | S | — | ethyl | (gum) |
| Cl | NO₂ | CH₃ | CH₂ | S | — | n-butyl | (gum) |
| CH₃O | CN | CH₃ | CH₂ | S | — | phenyl | (gum) |
| CH₃ | CN | CH₃ | CH₂ | S | — | phenyl | 98–99 |
| CF₃ | NO₂ | CH₃ | CH₂ | S | CH₂ | phenyl | 79–80 |
| CF₃ | NO₂ | CH₃ | CH₂CH₂ | S | — | phenyl | (gum) |
| CF₃ | CN | CH₃ | CH₂CH₂ | S | — | phenyl | 115–116.5 |
| CF₃ | CN | CH₃ | CH₂ | S | CH₂ | phenyl | 105–106 |
| Cl | CN | CH₃ | CH₂ | S | CH₂ | phenyl | 123–124 |
| CF₃ | NO₂ | CH₃ | CH₂ | O | — | phenyl | 118–119 |
| CF₃ | CN | CH₃ | CH₂ | O | — | phenyl | (gum) |
| CF₃ | NO₂ | CF₃ | CH₂ | S | — | phenyl | 139–140 |
| CF₃ | NO₂ | CF₃ | CH₂ | S | — | 4-chlorophenyl | 147–148 |
| CF₃ | NO₂ | CF₃ | CH₂ | S | — | 4-nitrophenyl | 145–146 |
| CF₃ | NO₂ | CF₃ | CH₂ | S | — | methyl | 82–85 |
| CF₃ | NO₂ | CF₃ | CH₂ | S | — | ethyl | 79–81 |
| CF₃ | NO₂ | CF₃ | CH₂ | S | — | n-propyl | 67–68 |
| CF₃ | NO₂ | CF₃ | CH₂ | S | — | isopropyl | 88–89 |
| CF₃ | CN | CF₃ | CH₂ | S | — | phenyl | 143–144 |
| CF₃ | CN | CF₃ | CH₂ | S | — | 4-chlorophenyl | 178–179 |
| CF₃ | CN | CF₃ | CH₂ | S | — | methyl | 120.5–122 |
| CF₃ | CN | CF₃ | CH₂ | S | — | ethyl | 119–120 |
| CF₃ | CN | CF₃ | CH₂ | S | — | n-propyl | 88–90 |
| CF₃ | CN | CF₃ | CH₂ | S | — | isopropyl | 107–109 |
| Cl | Cl | CF₃ | CH₂ | S | — | phenyl | 104 |
| Cl | Cl | CF₃ | CH₂ | S | — | methyl | 84–85 |
| Cl | Cl | CF₃ | CH₂ | S | — | ethyl | 57–59 |
| Cl | Cl | CF₃ | CH₂ | S | — | n-propyl | 60–61 |
| Cl | Cl | CF₃ | CH₂ | S | — | isopropyl | 57–59 |
| Cl | CN | CF₃ | CH₂ | S | — | phenyl | 152 |
| Cl | CN | CF₃ | CH₂ | S | — | methyl | 121–122.5 |
| Cl | CN | CF₃ | CH₂ | S | — | ethyl | 95–96 |
| Cl | CN | CF₃ | CH₂ | S | — | n-propyl | 89–90 |
| Cl | CN | CF₃ | CH₂ | S | — | isopropyl | 87–88 |
| CF₃ | NO₂ | CF₃ | CH₂ | S | CH₂ | phenyl | 120–121 |
| CF₃ | CN | CF₃ | CH₂ | S | CH₂ | phenyl | 138–139 |
| Cl | Cl | CF₃ | CH₂ | S | CH₂ | phenyl | 145–146 |

All the anilines used as starting materials are known compounds. The 2-hydroxy-substituted-alkanoic acids were obtained either by the process described in the second part of Example 1 (Route A), or by the process exemplified below (Route B). Those acids which are novel and which were characterised by melting point are described in the table below:

Route B 1,1,1-Trifluoro-3-phenylthiopropan-2-one (13.1 g.) was added dropwise to a cooled stirred solution of potassium cyanide (4.4 g.) in water (16 ml.) at such a rate that the temperature of the mixture was maintained at between 0° and 5° C. A 4:1 v/v mixture of water and concentrated sulphuric acid (17.1 ml.) was added at such a rate as to maintain the above temperature, and the mixture was then stirred at laboratory temperature for 15 hours and then extracted three times with diethyl ether (25 ml. each time). The combined extracts were washed three times with water (25 ml. each time), dried over magnesium sulphate and evaporated to dryness under reduced pressure.

A mixture of the cyanhydrin thus obtained (3.0 g.) and concentrated aqueous hydrochloric acid (30 ml.) was heated in a sealed tube at 110° C. for 6 hours, cooled and poured onto ice. The aqueous mixture was extracted four times with diethyl ether (25 ml. each time) and the combined ethereal solutions were extracted twice with saturated aqueous sodium bicarbonate solution (40 ml. each time). The combined extracts were acidified with aqueous hydrochloric acid and then extracted twice with diethyl ether (40 ml. each time). The combined extracts were dried over magnesium sulphate and evaporated to dryness and the residue was stirred with petroleum ether (b.p. 60°–80° C.). The mixture was filtered and there was thus obtained as solid residue 2-hydroxy-3-phenylthio-2-trifluoromethylpropionic acid, m.p. 83°–84° C.

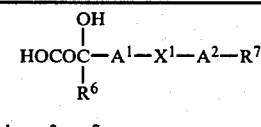

| R⁶ | A¹ | X¹ | A² | R⁷ | Route | m.p (°C.) |
|---|---|---|---|---|---|---|
| CH₃ | CH₂ | S | — | 2-nitrophenyl | B | 85–88 |
| CH₃ | CH₂ | S | — | methyl | A | 48–52 |
| CH₃ | CH₂ | S | — | isopropyl | A | 50–52 |
| CH₃ | CH₂ | S | CH₂ | phenyl | A | 62–63 |
| CH₃ | CH₂ | O | — | phenyl | A | 128–130 |
| CF₃ | CH₂ | S | — | 4-nitrophenyl | B | 169–171* |
| CF₃ | CH₂ | S | — | methyl | B | 73–76 |
| CF₃ | CH₂ | S | — | n-propyl | B | 37–40 |
| CF₃ | CH₂ | S | — | isopropyl | B | 57–59 |
| CF₃ | CH₂ | S | CH₂ | phenyl | B | 91–92 |

*m.p. of dicyclohexylamine salt used for characterisation.

The thio-alkanones used in Route B were prepared by the reaction of the appropriate thiol with the appropriate bromoketone by conventional means (for example as described in Zhur.org.Khim., 1971, 7, 2221). Those which are novel and were characterised are described in the following table:

| | CF₃COCH₂S—A²—R⁷ | |
|---|---|---|
| A² | R⁷ | b.p. (°C./mm.Hg.) |
| — | 4-nitrophenyl | 84.5–86 (m.p.) |
| — | methyl | 39–47/100 |
| — | n-propyl | 72–82/65 |
| — | isopropyl | 75–85/87 |
| CH₂ | phenyl | 118–122/17 |

EXAMPLE 3

A solution of ethanethiol (0.45 ml.) in tetrahydrofuran (5 ml.) was added dropwise to a stirred suspension of sodium hydride (0.28 g. of a 60% dispersion in mineral oil) in tetrahydrofuran (10 ml.) which was maintained at 0°-5° C., and the mixture was then stirred at laboratory temperature for 15 minutes. A solution of 3,4-dichloro-N-(2,3-epoxy-2-methylpropionyl)aniline (1.5 g.) in tetrahydrofuran (15 ml.) was added dropwise and the mixture was stirred at laboratory temperature for 15 hours. Water (50 ml.) was added, the organic layer was separated and the aqueous layer was extracted twice with diethyl ether (25 ml. each time). The combined organic solutions were dried over magnesium sulphate and evaporated to dryness under reduced pressure. The residue was purified by flash-chromatography on silica gel (Merck 9385) using a 1:1 v/v mixture of ethyl acetate and petroleum ether (b.p. 60°-80° C.) as eluant. The product was crystallised from a 5:1 v/v mixture of toluene and petroleum ether (b.p. 60°-80° C.) and there was thus obtained 3,4-dichloro-N-(3-ethylthio-2-hydroxy-2-methylpropionyl)aniline, m.p. 81°-83° C.

The 3,4-dichloro-N-(2,3-epoxy-2-methylpropionyl)aniline used as starting material was obtained as follows:

A solution of 3,4-dichloroaniline (10 g.) in dimethylacetamide (25 ml.) was added dropwise to a stirred, cooled solution of methacryloyl chloride (10 ml.) in dimethylacetamide (50 ml.) at such a rate that the internal temperature of the mixture did not exceed 0° C., and the mixture was then stirred at laboratory temperature for 16 hours and then poured into cold water (1 liter). The mixture was extracted 5 times with diethyl ether (100 ml. each time) and the combined extracts were dried and evaporated to dryness. The residue was crystallised from a 1:1 v/v mixture of toluene and petroleum ether (b.p. 60°-80° C.) at −50° C., and there was thus obtained 3,4-dichloro-N-methacryloylaniline, m.p. 120°-122° C.

m-Chloroperbenzoic acid (3.4 g.) was added portionwise to a boiling solution of 3,4-dichloro-N-methacryloylaniline (2.2 g.) and 4-methyl-2,6-di-t-butylphenol (0.05 g.) in 1,1,1-trichloroethane (75 ml.) and the mixture was heated under reflux for 4 hours, cooled and washed successively (25 ml. portions each time) once with saturated aqueous sodium sulphite solution, twice with saturated aqueous sodium bicarbonate solution and once with saturated sodium chloride solution, dried over magnesium sulphate and evaporated to dryness. The residue was purified by chromatography on a silica gel (Merck 7734) column using a 1:1 v/v mixture of ethyl acetate and petroleum ether (b.p. 60°-80° C.) as eluant. The product was crystallised from petrolum ether (b.p, 60°-80° C.) and there was thus obtained 3,4-dichloro-N-(2,3-epoxy-2-methylpropionyl)aniline, m.p. 90°-92° C.

EXAMPLE 4

The process described in Example 3 was repeated using the appropriate thiol and the appropriate N-(2,3-epoxy-2-methylpropionyl)aniline as starting materials, and there were thus obtained the compounds described in the followilg table:

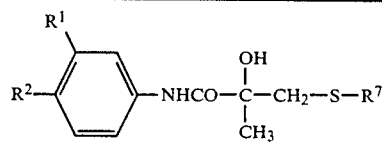

| $R^1$ | $R^2$ | $R^7$ | m.p. (°C.) |
| --- | --- | --- | --- |
| Cl | Cl | thiazol-2-yl | 105–107 |
| Cl | Cl | pyrimidin-2-yl | 103–105 |
| CF$_3$ | NO$_2$ | 2-chlorophenyl | 98–100 |
| CF$_3$ | NO$_2$ | 3-chlorophenyl | 132–133 |
| CF$_3$ | NO$_2$ | 4-chlorophenyl | 101–103 |
| CF$_3$ | NO$_2$ | 4-fluorophenyl | 112–113 |
| CF$_3$ | NO$_2$ | 4-cyanophenyl | 108–111 |
| CF$_3$ | NO$_2$ | 4-nitrophenyl | 139–141 |
| CF$_3$ | NO$_2$ | 4-methoxyphenyl | 120–121 |
| CF$_3$ | NO$_2$ | 4-methylthiophenyl | 111–112 |
| CF$_3$ | NO$_2$ | n-pentyl | (oil) |
| CF$_3$ | NO$_2$ | 2-hydroxyethyl | (oil) |
| CF$_3$ | NO$_2$ | allyl | 80–81 |
| CF$_3$ | NO$_2$ | 2-methylallyl | 78–79 |
| CF$_3$ | NO$_2$ | cyclopentyl | 87–88.5 |
| CF$_3$ | NO$_2$ | pyrid-2-yl | 155–157 |
| CF$_3$ | NO$_2$ | pyrid-3-yl | 149–150 |
| CF$_3$ | NO$_2$ | pyrid-4-yl | 193–195 |
| CF$_3$ | NO$_2$ | 6-chloropyrid-2-yl | 159–162 |
| CF$_3$ | NO$_2$ | thiazol-2-yl | 131–132 |
| CF$_3$ | NO$_2$ | 4-methylthiazol-2-yl | 160–162 |
| CF$_3$ | NO$_2$ | 5-methyl-1,3,4-thiadiazol-2-yl | 109–111 |
| CF$_3$ | CN | 4-chlorophenyl | 137–138 |
| CF$_3$ | CN | 4-fluorophenyl | 116–117 |
| CF$_3$ | CN | 4-methylthiophenyl | 125–126 |
| CF$_3$ | CN | pyrid-2-yl | 137–139 |
| CF$_3$ | CN | pyrid-3-yl | 135–136 |
| CF$_3$ | CN | 5-chloropyrid-2-yl | 113–115 |
| CF$_3$ | CN | thien-2-yl | 101–103 |
| CF$_3$ | CN | thiazol-2-yl | 107–109 |
| CF$_3$ | CN | 4,5-dihydrothiazol-2-yl | 110–111 |
| CF$_3$ | CN | 1-methylimidazol-2-yl | 112 |
| CF$_3$ | CN | benzthiazol-2-yl | 178–180 |
| CF$_3$ | CN | pyrimidin-2-yl | 120–121 |

Similarly, by using the appropriate thiol and the apropriate N-(2,3-epoxy-2-methylbutyryl)aniline there were obtained:

4-cyano-3-trifluoromethyl-N-[(2SR,3RS)-3-p-fluorophenylthio-2-hydroxy-2-methylbutyryl]aniline, m.p. 114°–116° C. and 4-nitro-3-trifluoromethyl-N-[(2SR,3RS)-2-hydroxy-2-methyl-3-phenylthiobutyryl]aniline, m.p. 143°–145° C.

The N-(2,3-epoxy-2-methylpropionyl or butyryl)anilines used as starting material were obtained by the epoxidation of the appropriate N-methacryloyl or N-methylcrotonoylaniline by a similar process to that described in the second part of Example 3. N-Methacryloyl-4-nitro-3-trifluoromethylaniline had m.p. 102°–104° C. and the corresponding epoxy compound had m.p. 119°–121° C.;

4-cyano-N-methacryloyl-3-trifluoromethylaniline had m.p. 137°–139° C. and the corresponding epoxy compound had m.p. 149°–150° C.

N-(2-methylcrotonoyl)-4-nitro-3-trifluoromethylaniline had m.p. 65°–67° C. and the corresponding epoxy compound had m.p. 99°–102° C.;

4-cyano-N-(2-methylcrotonoyl)-3-trifluoromethylaniline had m.p. 127°–128° C. and the corresponding epoxy compound had m.p. 100°–103° C.

(The last two compounds are derived from transtiglic acid as opposed to cis-angelic acid).

EXAMPLE 5

A solution of sodium metaperiodate (0.407 g.) in water (15 ml.) was added dropwise to a stirred solution of 4-cyano-3-trifluoromethyl-N-(3-ethylthio-2-hydroxy-2-trifluoromethylpropionyl)aniline (0.6 g.) in methanol (25 ml.) and the mixture was stirred at laboratory temperature for 48 hours and then filtered. The solid was washed with methanol (25 ml.) and the mixture was filtered, and the combined filtrates were evaporated to dryness under reduced pressure. The residue was dissolved in ethyl acetate (150 ml.) and the solution was washed successively with water (15 ml.), saturated aqueous sodium sulphite solution (25 ml.) and saturated aqueous sodium chloride solution (25 ml.), dried over magnesium sulphate and evaporated to dryness under reduced pressure. The residue was chromatographed on silica gel (Merck 7734) using a 1:1 v/v mixture of ethyl acetate and petroleum ether (b.p. 60°–80° C.) as eluant, and the two diastereoisomers of 4-cyano-3-trifluoromethyl-N-(3-ethylsulphinyl-2-hydroxy-2-trifluoromethylpropionyl)aniline were obtained by evaporation of the appropriate fractions of the eluate. These had m.p. 141°–143° C. (more polar isomer) and 160°–162° C. (less polar isomer).

The process described above was repeated using the appropriate thiopropionylaniline as starting material, and there were thus obtained the compounds described in the following table:

$$R^2 \text{—} \underset{R^1}{\text{C}_6\text{H}_3} \text{—NHCO—} \underset{R^6}{\overset{\text{OH}}{\text{C}}} \text{—CH}_2\text{—SO—R}^7$$

| $R^1$ | $R^2$ | $R^6$ | $R^7$ | Diastereo-isomer | m.p. (°C.) |
|---|---|---|---|---|---|
| $CF_3$ | $NO_2$ | $CH_3$ | phenyl | more polar | 126.5–127.5 |
| $CF_3$ | CN | $CH_3$ | phenyl | more polar | 164–165 |
| $CF_3$ | CN | $CF_3$ | phenyl | mixed | 175–176 |
| $CF_3$ | CN | $CH_3$ | ethyl | mixed | 110–112 |

EXAMPLE 6

A solution of m-chloroperbenzoic acid (0.40 g.) in methylene chloride (80 ml.) was added to a stirred solution of 4-cyano-3-trifluoromethyl-N-(2-hydroxy-3-phenylthio-2-trifluoromethylpropionyl)aniline (0.38 g.) in methylene chloride (100 ml.) during 30 minutes and the reaction mixture was then stirred at laboratory temperature for 18 hours. Aqueous 10% w/v sodium sulphite gel solution (15 ml.) was added, the mixture was stirred and the organic layer was separated, washed successively twice with aqueous 10% w/v sodium carbonate solution (15 ml. each time) and once with saturated aqueous sodium chloride solution (15 ml.), dried over anhydrous magnesium sulphate and evaporated to dryness. The residue was dissolved in a 1:1 v/v mixture of ethyl acetate and petroleum ether (b.p. 60°–80° C.) and the solution was chromatographed on a silica gel column (Merck 7734) using a 1:1 v/v mixture of ethyl acetate and petroleum ether (b.p. 60°–80° C.) as eluant. There was thus obtained 4-cyano-3-trifluoromethyl-N-(2-hydroxy-3-phenylsulphonyl-2-trifluoromethylpropionyl)aniline, m.p. 175°–176° C.

The process described above was repeated using the appropriate thiopropionylaniline as starting material and there were thus obtained the compounds described in the following table:

$$R^2 \text{—} \underset{R^1}{\text{C}_6\text{H}_3} \text{—NHCO—} \underset{R^6}{\overset{\text{OH}}{\text{C}}} \text{—CH}_2\text{—SO}_2\text{—R}^7$$

| $R^1$ | $R^2$ | $R^6$ | $R^7$ | m.p. (°C.) |
|---|---|---|---|---|
| $CF_3$ | $NO_2$ | $CH_3$ | phenyl | 149–151 |
| $CF_3$ | $NO_2$ | $CH_3$ | 4-fluorophenyl | 188–189 |
| $CF_3$ | $NO_2$ | $CH_3$ | pyrid-2-yl | 148–150 |
| $CF_3$ | $NO_2$ | $CH_3$ | ethyl | 135–136 |
| $CF_3$ | $NO_2$ | $CH_3$ | n-propyl | 118–119 |
| $CF_3$ | $NO_2$ | $CH_3$ | n-pentyl | 104–105 |
| $CF_3$ | CN | $CH_3$ | phenyl | 172–173.5 |
| $CF_3$ | CN | $CH_3$ | 4-fluorophenyl | 189–191 |
| $CF_3$ | CN | $CH_3$ | ethyl | 116–118 |
| $CF_3$ | CN | $CH_3$ | n-propyl | 117–119 |
| $CF_3$ | CN | $CF_3$ | ethyl | 164–165 |
| Cl | $NO_2$ | $CH_3$ | ethyl | 145–146 |
| Cl | $NO_2$ | $CH_3$ | n-butyl | 116–118 |
| Cl | CN | $CH_3$ | ethyl | 135–136 |
| $CH_3O$ | CN | $CH_3$ | phenyl | 172–173 |

EXAMPLE 7

(−)-Camphanoyl chloride (4.33 g.) was added portionwise during 5 minutes to a solution of 4-cyano-3-trifluoromethyl-N-(2-hydroxy-3-phenylthio-2-trifluoromethylpropionyl)aniline (5.8 g.) in pyridine (35 ml.) and the mixture was heated at 95° C. for 150 minutes and then evaporated to dryness. Toluene (50 ml.) was added and the mixture was again evaporated to dryness. The residue was dissolved in ethyl acetate (200 ml.) and the solution was washed with water (30 ml.) and then twice with saturated aqueous sodium chloride solution (20 ml. each time), dried over magnesium sulphate and evaporated to dryness under reduced pressure. The residue was dissolved in methylene chloride (10 ml.) and the solution was flash chromatographed on silica gel (Merck 9385) using methylene chloride as eluant. There were thus obtained the two disastereoisomers of 4-cyano-3-trifluoromethyl-N-[2-(−)-camphanoyloxy-3-phenylthio-2-trifluoromethylpropionyl)aniline, the less polar isomer having m.p. 121°–123° C. and the more polar isomer having m.p. 140°–143° C.

A mixture of a solution of the less polar isomer (2.0 g.) in methanol (30 ml.) and aqueous 4% w/v sodium hydroxide solution (3.5 ml.) was stirred at laboratory temperature for 30 minutes and then evaporated to dryness under reduced pressure. The residue was dissolved in ethyl acetate (160 ml.) and the solution was washed successively with water (25 ml.), saturated aqueous sodium chloride solution (25 ml.), aqueous 2N-hydrochloric acid (15 ml.), water (25 ml.) and saturated aqueous sodium chloride solution (25 ml.), dried over magnesium sulphate and evaporated to dryness. The residue was dissolved in methylene chloride (5 ml.) and flash-chromatographed on silica gel (Merck 9385) using methylene chloride as eluant. The product was crystallised from petroleum ether (b.p. 60°–80° C.) and there was thus obtained (−)-4-cyano-3-trifluoromethyl-N-(2-hydroxy-3-phenylthio-2-trifluoromethylpropionyl)aniline, m.p. 156°–157° C., $[\alpha]_D^{25} = 43.8°$ (C, 1% in methanol).

The process described in the preceding paragraph was repeated using the more polar isomer of the camphanoyl ester, and the product obtained was crystallised from a 5:1 v/v mixture of toluene and petroleum ether (b.p 60°-80° C.). There was thus obtained (+)-4-cyano-3-trifluoromethyl-N-(2-hydroxy-3-phenylthio-2-trifluoromethylpropionyl)aniline, m.p. 159°-160° C., $[\alpha]_D^{23} = +45.5°$ (C, 1% in methanol).

EXAMPLE 8

The process described in Example 7 was repeated using 4-cyano-3-trifluoromethyl-N-(3-p-fluorophenylthio-2-hydroxy-2-methylpropionyl)aniline as the compound to be resolved. There were thus obtained the (−)-isomer, m.p. 94°-96° C., $[\alpha]_D^{24} = -3.06°$ (C, 1% in methanol) and the (+)-isomer, m.p. 95°-97° C., $[\alpha]_D^{24} = +2.42°$ (C, 1% in methanol).

EXAMPLE 9 n-Butyl-lithium (4.7 ml. of a 1.6 molar solution in hexane) was added during 2 minutes to a stirred solution of methylthiobenzene (0.82 ml.) and 1,4-diazabicyclo[2,2,2]octane (0.78 g.) in tetrahydrofuran (20 ml.) which was maintained at −2° C. under an atmosphere of argon. The mixture was allowed to warm up to +2° C., stirred at that temperature for 2 hours, cooled to −65° C. and a solution of N-(3,4-dichlorophenyl)-pyruvamide (0.81 g.) in tetrahydrofuran (5 ml) was added during 5 minutes.

The mixture was stirred and allowed to warm up to −30° C. during 90 minutes, aqueous 2N-hydrochloric acid (25 ml.) was added, the tetrahydrofuran was removed by evaporation under reduced pressure and the residue was extracted three times with diethyl ether (40 ml. each time). The combined extracts were washed with saturated aqueous sodium chloride solution, dried and evaporated to dryness and the residue was purified by flash chromatography on a silica gel column (Merck 9385) using a 5:2 v/v mixture of petroleum ether (b.p. 60°-80° C.) and ethyl acetate as eluant. The product was crystallised from petroleum ether (b.p. 60°-80° C.) and there was thus obtained 3,4-dichloro-N-( 2-hydroxy-2-methyl-3-phenylthiopropionyl)aniline, m.p. 85°-86° C.

The process described above was repeated using 4-bromo-2-methylsulphonylthiophen as starting material in place of methylthiobenzene. There was thus obtained N-[3-(4-bromothien-2-ylsulphonyl)-2-hydroxy-2-methylpropionyl]-3,4-dichloroaniline, m.p. 170°-171° C.

EXAMPLE 10

A solution of N-methylaniline (0.38 ml.) in tetrahydrofuran (2 ml.) as added to a stirred suspension of sodium hydride (0.17 g. of a 50% dispersion in mineral oil) in tetrahydrofuran (4 ml.) which was maintained under an atmosphere of argon, the mixture was stirred at laboratory temperature for 1 hour and a solution of N-(2,3-epoxy-2-methylpropionyl)-4-nitro-3-trifluoromethylaniline (1.0 g.) in tetrahydrofuran (10 ml.) was added dropwise. The mixture was stirred at laboratory temperature for 16 hours, then at 100° C. for 1 hour, cooled and water (50 ml.) was added. The mixture was extracted three times with ethyl acetate (30 ml. each time) and the combined extracts were washed with saturated aqueous sodium chloride solution, dried and evaporated to dryness. The residue was purified by chromatography on a silica gel column (Merck 7734) using a 1:1 v/v mixture of ethyl acetate and petroleum ether (b.p. 60°-80° C.), and there was thus obtained N-(2-hydroxy-2-methyl-3-N-methylanilinopropionyl)-4-nitro-3-trifluoromethylaniline, m.p. 121°-124° C.

What we claim is:

1. An acylanilide of the formula:

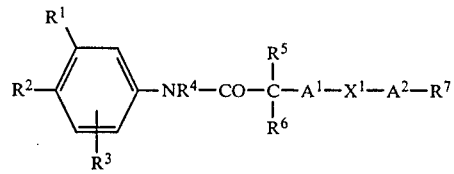

wherein $R^1$ is cyano, nitro, fluoro, chloro, bromo or iodo, or alkyl, alkoxy, alkanoyl, alkylthio, alkylsulphinyl, alkylsulphonyl or perfluoroalkyl each of up to 4 carbon atoms;

wherein $R^2$ is cyano, nitro, fluoro, chloro, bromo or iodo, or alkanoyl, alkylthio, alkylsulphinyl, alkysulphonyl or perfluoroalkyl, each of up to 4 carbon atoms;

wherein $R^3$ is hydrogen or halogen;

wherein $R^4$ is hydrogen or alkyl or up to 4 carbon atoms;

wherein $R^5$ is hydroxy or alkoxy or acyloxy each of up to 15 carbon atoms;

wherein $R^6$ is alkyl or halogenoalkyl of up to 4 carbon atoms;

wherein $A^1$ is alkylene of up to 6 carbon atoms;

wherein $A^2$ is a direct link or alkylene of up to 6 carbon atoms;

wherein $X^1$ is sulphur, sulphinyl or sulphonyl (—$SO_2$—);

wherein $R^7$ is alkyl, alkenyl, hydroxyalkyl or cycloalkyl each of up to 6 carbon atoms, or $R^7$ is phenyl which bears one or two substituents selected from hydrogen, halogen, nitro, and cyano, and alkyl, alkoxy, alkanoyl, alkylthio, alkylsulphinyl, alkylsulphonyl and perfluoroalkyl; or $R^7$ is naphthyl; or $R^7$ is 5- or 6-membered saturated or unsaturated heterocyclic which contains one, two or three heteroatoms selected from oxygen, nitrogen and sulphur, which heterocyclic may be a single ring or may be fused to a benzo-ring, and which heterocyclic is unsubstituted or bears one or two halogen or alkyl of up to 4 carbon atoms substituents.

2. An acylanilide as claimed in claim 1 wherein $R^1$ is cyano, nitro, trifluoromethyl, chloro, methyl or methoxy, $R^2$ is cyano, nitro, trifluoromethyl or chloro, $R^3$ and $R^4$ are both hydrogen, $R^5$ is hydroxy, $R^6$ is methyl or trifluoromethyl, $A^1$ is methylene, ethylene or ethylidene, $X^1$ is sulphur, sulphinyl or sulphonyl, $A^2$ is a direct link or methylene and $R^7$ is alkyl, alkenyl, hydroxyalkyl or cycloalkyl each of up to 6 carbon atoms, or phenyl which is unsubstituted or which bears one fluoro, chloro, cyano, nitro, methoxy or methylthio substitutent, or thienyl, imidazolyl, thiazolyl, benzothiazolyl, thiadiazolyl, pyridyl or pyrimidinyl which is unsubstituted or which bears one chloro, bromo or methyl substitutent.

3. An acylanilide as claimed in claim 1 wherein $R^1$ is trifluoromethyl, $R^2$ is cyano or nitro, $R^3$ and $R^4$ are both hydrogen, $R^5$ is hydroxy, $R^6$ is methyl, $A^1$ is methylene, $X^1$ is sulphur, sulphinyl or sulphonyl, $A^2$ is a direct link and $R^7$ is alkyl of up to 3 carbon atoms, or is allyl, phenyl, p-fluorophenyl, thiazol-2-yl, 4-methylthiazol-2-yl, 5-methyl-1,3,4-thiadiazol-2-yl or 2-pyridyl.

4. A compound selected from the group consisting of 3-chloro-4-cyano-N-(3-ethylthio-2-hydroxy-2-methylpropionyl)-aniline;
3-chloro-4-cyano-N-(3-ethylsulphonyl-2-hydroxy-2-methylpropionyl)aniline;
4-cyano-3-trifluoromethyl-N-(2-hydroxy-2-methyl-3-phenylsulphonylpropionyl)aniline;
4-cyano-3-trifluoromethyl-N-(3-ethylsulphonyl-2-hydroxy-2-methylpropionyl)aniline;
4-nitro-3-trifluoromethyl-N-(2-hydroxy-3-phenylsulphonyl-2-methylpropionyl)aniline;
4-nitro-3-trifluoromethyl-N-(3-ethylsulphonyl-2-hydroxy- 2-methylpropionyl)aniline;
3-chloro-4-nitro-N-(2-hydroxy-3-phenylthio-2-methylpropionyl)aniline;
4-nitro-3-trifluoromethyl-N-[2-hydroxy-2-methyl-3-(thiazol-2-ylthio)propionyl]aniline;
4-nitro-3-trifluoromethyl-N-[3-allylthio-2-hydroxy-2-methylpropionyl)aniline;
4-nitro-3-trifluoromethyl-N-(3-p-fluorophenylthio-2-hydroxy-2-methylpropionyl)aniline;
4-nitro-3-trifluoromethyl-N-[2-hydroxy-2-methyl-3-(pyrid-2-ylthio)propionyl]aniline;
4-nitro-3-trifluoromethyl-N-[2-hydroxy-2-methyl-3-(5-methyl-1,3,4-thiadiazol-2-ylthio)propionyl]aniline;
4-nitro-3-trifluoromethyl-N-[2-hydroxy-2-methyl-3-(4-methylthiazol-2-ylthio)propionyl]aniline;
4-nitro-3-trifluoromethyl-N-[2-hydroxy-2-methyl-3-(pyrid-2-ylsulphonyl)propionyl]aniline;
4-nitro-3-trifluoromethyl-N-(3-p-fluorophenylsulphonyl-4-hydroxy-2-methylpropionyl)aniline;
4-cyano-3-trifluoromethyl-N-[2-hydroxy-2-methyl-3-(thiazol-2-ylthio)propionyl]aniline;
4-cyano-3-trifluoromethyl-N-[2-hydroxy-2-methyl-4-(pyrid-2-ylthio)propionyl]aniline;
4-cyano-3-trifluoromethyl-N-(2-hydroxy-2-methyl-3-methylthiopropionyl)aniline; and
4-cyano-3-trifluoromethyl-N-(3-p-fluorophenylthio-2-hydroxy-2-methylpropionyl)aniline.

5. The compound 4-cyano-3-trifluoromethyl-N-(3-p-fluorophenylsulphonyl-2-hydroxy-2-methylpropionyl)aniline.

6. A pharmaceutical or veterinary composition which comprises an acylanilide, claimed in claim 1, in association with a pharmaceutically-acceptable diluent or carrier.

7. A composition as claimed in claim 6 which is in a form suitable for oral dosage, as a tablet, capsule, aqueous or oily solution or suspension or emulsion; or in the form of a sterile solution or suspension suitable for parenteral administration; or in the form of an ointment or lotion for topical administration, or in the form of a suppository for anal or vaginal administration.

8. A composition as claimed in claim 6 which additionally contains one or more drugs selected from anti-oestrogens, aromatase inhibitors, progestins, inhibitors of gonadotrophin secretion, LH-RH-analogues, cytotoxic agents, antibiotics and anti-inflammatory agents.

9. A method for producing an antiandrogenic effect in a warm-blooded animal in need of such treatment which comprises administering to said animal an effective amount of acylanilide claimed in claim 1.

* * * * *

UNITED STATES PATENT AND TRADEMARK OFFICE

CERTIFICATE EXTENDING PATENT TERM
UNDER 35 U.S.C. § 156

PATENT NO.      :   4,636,505

ISSUED          :   January 13, 1987

INVENTOR(S)     :   Howard Tucker

PATENT OWNER    :   Zeneca Limited

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of 1,723 days from the original expiration date of the patent, January 13, 2004, with all rights pertaining thereto as provided by 35 U.S.C. § 156(b).

I have caused the seal of the Patent and Trademark Office to be affixed this 21st day of April 1997.

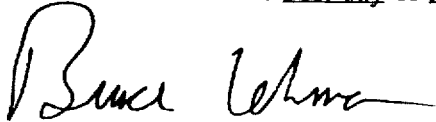

Bruce A. Lehman
Assistant Secretary of Commerce and
Commissioner of Patents and Trademarks